United States Patent
Lincoln et al.

(10) Patent No.: US 11,860,092 B2
(45) Date of Patent: Jan. 2, 2024

(54) PROTECTIVE COVER FOR CHAMBERLESS POINT SENSOR

(71) Applicant: Kidde Technologies, Inc., Wilscon, NC (US)

(72) Inventors: David L. Lincoln, Johnston, RI (US); Michael J. Birnkrant, Wethersfield, CT (US); Kenneth Bell, Epsom (GB); Peter R. Harris, West Hartford, CT (US); Jennifer M. Alexander, Glastonbury, CT (US)

(73) Assignee: Kidde Technologies, Inc., Wilson, NC (US)

( * ) Notice: Subject to any disclaimer, the term of this patent is extended or adjusted under 35 U.S.C. 154(b) by 0 days.

(21) Appl. No.: 17/469,470

(22) Filed: Sep. 8, 2021

(65) Prior Publication Data

US 2021/0404955 A1  Dec. 30, 2021

Related U.S. Application Data (62) Division of application No. 15/936,073, filed on Mar. 26, 2018, now abandoned.

(51) Int. Cl.
*G01N 21/53* (2006.01)
*G01N 21/01* (2006.01)
(Continued)

(52) U.S. Cl.
CPC ............. *G01N 21/53* (2013.01); *G01N 21/01* (2013.01); *G01N 33/0027* (2013.01);
(Continued)

(58) Field of Classification Search
CPC ........... G01N 2021/0106; G01N 21/01; G01N 21/53; G01N 33/0027; G08B 17/107; G08B 17/113; B65B 1/04
See application file for complete search history.

(56) References Cited

U.S. PATENT DOCUMENTS 4,018,513 A * 4/1977 Boeke .................. G08B 17/103
359/894
4,786,811 A * 11/1988 Sasaki .................. G08B 17/113
250/385.1
(Continued)

FOREIGN PATENT DOCUMENTS

CN  204630924 U  9/2015
DE  19912911 A1  10/2000
(Continued)

OTHER PUBLICATIONS

Extended European Search Report dated Jul. 16, 2019, recieved for corresponding European Application No. 19164852.6.
(Continued)

*Primary Examiner* — Violeta A Prieto
(74) *Attorney, Agent, or Firm* — Kinney & Lange, P.A.

(57) ABSTRACT

A covered chamberless particulate detector includes a chamberless detector configured to produce a signal when particulate sensing events occurs, one or more optical emitters configured to emit one or more emitting cones of light, one or more optical sensors defining one or more receiving cones and configured to detect occurrence of particulate sensing events, and a protective cover defining an inside region and an outside region. Each of the one or more emitting cones of light is configured to overlap with each of the one or more receiving cones, thereby creating one or more sensing volumes which may be in the inside region, the outside region, or both regions. The protective cover can be transparent, partially transparent, or opaque, and can include apertures. The optical emitters and detectors can use one or more wavelengths, allowing discrimination of various airborne particulates.

20 Claims, 4 Drawing Sheets

(51) Int. Cl.
   *G01N 33/00* (2006.01)
   *G08B 17/107* (2006.01)
   *G08B 17/113* (2006.01)

(52) U.S. Cl.
   CPC .......... *G08B 17/107* (2013.01); *G08B 17/113* (2013.01); *G01N 2021/0106* (2013.01)

(56) References Cited

U.S. PATENT DOCUMENTS

| | | | |
|---|---|---|---|
| 8,441,368 B2 * | 5/2013 | Liess | G01N 21/53 340/630 |
| 8,773,272 B2 | 7/2014 | Nagashima | |
| 9,201,051 B2 | 12/2015 | Lewiner | |
| 9,767,665 B2 * | 9/2017 | Allemann | H04B 10/60 |
| 10,677,714 B2 * | 6/2020 | Lincoln | G01N 21/15 |
| 2007/0097366 A1 | 5/2007 | Leboeuf et al. | |
| 2007/0170352 A1 | 7/2007 | Fouquet et al. | |
| 2008/0018485 A1 | 1/2008 | Kadwell et al. | |
| 2008/0258925 A1 * | 10/2008 | Siber | G08B 29/24 340/630 |
| 2010/0309013 A1 * | 12/2010 | Liess | G08B 17/107 359/833 |
| 2011/0194111 A1 | 8/2011 | Dohi | |
| 2015/0346086 A1 | 12/2015 | Erdtmann | |
| 2016/0343226 A1 | 11/2016 | Fischer et al. | |
| 2017/0178481 A1 | 6/2017 | Zribi et al. | |
| 2019/0293556 A1 * | 9/2019 | Lincoln | G01N 21/53 |
| 2019/0383729 A1 * | 12/2019 | Lincoln | G01N 21/15 |

FOREIGN PATENT DOCUMENTS

| | | |
|---|---|---|
| DE | 102004001699 A1 | 8/2005 |
| DE | 102006006418 A1 | 8/2007 |
| DE | 102013003614 A1 | 8/2014 |
| EP | 1191496 A1 | 3/2002 |
| EP | 1783713 A1 | 5/2007 |
| EP | 1887536 A1 | 2/2008 |
| GB | 2410085 A | 7/2005 |
| JP | 55036785 A | 3/1980 |
| JP | 2015191466 A | 11/2015 |
| JP | 2016200980 A | 12/2016 |
| WO | 2009036988 A1 | 3/2009 |

OTHER PUBLICATIONS

Extended European Search Report dated Nov. 12, 2019, received for European Application No. 19180405.3, 8 pages.
Extended European Search Report dated Oct. 22, 2019, received for corresponding European Application No. 19164852.6, 18 pages.
European Office Action dated Aug. 18, 2020, received for corresponding European Application No. 19164852.6, 5 pages.
Optical Coating, Wikipedia, 5 pages.

* cited by examiner

PROTECTIVE COVER FOR CHAMBERLESS POINT SENSOR

CROSS-REFERENCE TO RELATED APPLICATION(S)

This application is a divisional of U.S. patent application Ser. No. 15/936,073, entitled "Protective Cover for Chamberless Point Sensor" by David L. Lincoln, Michael J. Birnkrant, Kenneth Bell, Peter R. Harris, and Jennifer M. Alexander, filed Mar. 26, 2018. The specification of the above referenced application is incorporated herein by reference in its entirety.

BACKGROUND

The present disclosure relates generally to particulate monitors and smoke detectors, and more particularly, to a protective cover for a chamberless point sensor.

Smoke detectors play an important role in identifying smoke, ideally alarming as early as possible in the course of fire. Smoke detectors can use one or more sources of light as the source of the smoke detection scheme, and can use multiple wavelengths of light to help improve detection performance. For example, dual wavelengths of light, one being infrared and the other being visible, can be used in a smoke detector. A chamberless detector can provide improved sensing performance over designs that utilize a chamber, therefore resulting in the popularity of the chamberless design in high-performance applications. A chamberless detector can be referred to as a next-generation point sensor, because of its advanced design and its use in detecting smoke at a particular point of installation. A chamberless detector can also be referred to as a chanberless point sensor. A commercial aircraft is a non-limiting example of a high-performance application where a chamberless point sensor utilizing multiple wavelengths of light can be used. There are many factors that contribute to the need for a high-performance chamberless detector, with non-limiting examples including the desire to discern between steam or dust and the smoke particles from a fire, the desire to avoid nuisance alarms from food preparation, and the desire to detect smoke particles that can be produced from smoldering synthetic materials, often resulting in particle sizes smaller than 0.5 μm (microns) in diameter. Additionally, chamberless detectors utilizing multiple wavelengths of light can be used to monitor indoor air quality, where fine particles (particle sizes≤2.5 μm) and coarse particles (particle sizes≤10 μm) can be important.

Despite the many advantages of a chamberless detector, there are a few problems that need to be overcome. For example, in not having a chamber, there is not a well-protected volume that is free from interference or tampering. Additionally, the optical emitters of a next-generation point sensor can cast light into the surrounding environment, where it can be a source of annoyance. Moreover, the optical detectors of a next-generation point sensor can be prone to interference from ambient light sources emanating from the surrounding environment.

SUMMARY

According to one embodiment of the present disclosure, a covered chamberless particulate detector includes a chamberless detector configured to produce a signal when particulate sensing events occurs, one or more optical emitters on the chamberless detector configured to emit one or more emitting cones of light, one or more optical sensors on the chamberless detector defining one or more receiving cones, and a protective cover on the chamberless detector defining an inside region and an outside region. Each optical sensor is configured to detect the occurrence of particulate sensing events, and each of the one or more emitting cones of light is configured to overlap with each of the one or more receiving cones, thereby creating one or more sensing volumes.

According to another embodiment of the present disclosure, a method of using a covered chamberless particulate detector that includes one or more optical emitters, one or more optical sensors, and a protective cover over the optical emitters and the optical sensors that defines an inside region and an outside region. The method includes emitting one or more emitting cones of light from the one or more optical emitters, receiving light in one or more receiving cones by the one or more optical sensors, detecting particulate sensing events, and producing a signal denoting occurrence of the particular sensing events. The detecting is based on the presence of particulate material in one or more sensing volumes defined by an overlap of the one or more emitting cones of light and the one or more receiving cones, where the one or more sensing volumes are located in the inside region, the outside region, or both the inside region and the outside region.

DETAILED DESCRIPTION

The present disclosure provides a protective cover for a next generation chamberless point sensor. As used in this disclosure, the next generation chamberless point sensor can be referred to as a chamberless point sensor and monitor, covered chamberless particulate detector, or chamberless detector for short. As used in this disclosure, "particulate" will be used to describe all airborne particles that are detectable, which includes smoke. Moreover, the descriptions provided herein refer to the detection of airborne particulates by the interaction of light and the scattering of light to the optical detection circuitry of the chamberless detector. The operation of a chamberless detector can be referred to as monitoring, whereby the chamberless detector monitors for sensing events. A sensing event is when an electrical response occurs within the detection circuitry as a result of a photo interaction.

Figure 1:
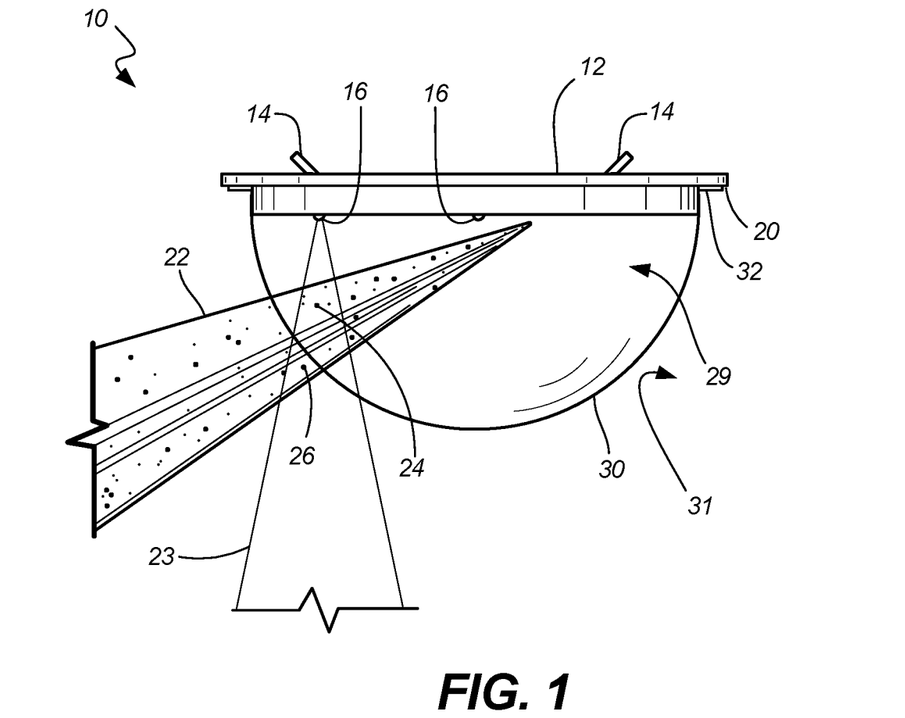
FIG. 1 is a side view of a next generation chamberless particulate detector with one embodiment of the protective cover.

FIG. 1 is a side view of a chamberless particulate detector with a protective cover. Shown in FIG. 1 are covered point sensor 10, chamberless detector 12, optical sources 14, optical sensors 16, mounting rim 20, emitting cone 22, receiving cone 23, near particles 24, far particles 26, inside region 29, protective cover 30, and outside region 31. As will be described in this disclosure, emitting cone 22 is associated with each optical source 14, and receiving cone 23 is associated with each optical sensor 16. The exemplary embodiment illustrated in FIG. 1 depicts two optical sources 14 and two optical sensors 16, but only one emitting cone 22 and one receiving cone 23 is shown for ease of illustration.

In the illustrated embodiment, covered point sensor 10 has a substantially hemispherical geometry, being comprised of chamberless detector 12 and protective cover 30. Chamberless detector 12 has a substantially flat profile as illustrated in the side view of FIG. 1. In the illustrated embodiment, chamberless detector 12 has a circular or disk-like shape viewed from the top or in perspective (not shown). In the illustrated embodiment, protective cover 30 has a semicircular shape as viewed from the side. Protective cover 30 can be referred to as an envelope, defining an inside region and an outside region of protective cover 30. In the illustrated embodiment, protective cover 30 has a diameter of about 10 cm (3.9 inches) in the region near where protective cover 30 attaches to chamberless detector 12. In other embodiments, protective cover 30 can have a diameter between 5-15 cm (2.0-5.9 inches). In yet other embodiments, protective cover 30 can have a diameter of less than 5 cm (2.0 inches), or greater than 15 cm (5.9 inches). In the illustrated embodiment, protective cover 30 has a generally hemispherical shape, in which the height of protective cover 30 is approximately half the diameter. In other embodiments, the geometry of protective cover 30 can be substantially different from hemispherical. For example, in an embodiment, protective cover 30 can be squat in its geometry, with a height less than approximately half the diameter. In another embodiment, the height of protective cover 30 can be significantly less than approximately half the diameter. Alternatively, in yet other embodiments, protective cover 30 can have a bulbous geometry, in which the height of protective cover 30 is greater than approximately half the diameter. In other embodiments, the cover can be cylindrical, square, or rectangular in shape, with these being non-limiting examples of possible geometries of protective cover 30.

In the illustrated embodiment, covered point sensor 10 includes chamberless detector 12 and protective cover 30. It will be appreciated that covered point sensor 10 can provide additional benefits including but not limited to reduction of transport time for particles to reach the particle detecting elements to enable faster alerting, alarm, and response by users and systems; improved sensitivity; improved manufacturability; negligible directionality; ease of maintenance; and enhanced aesthetic appearance.

Optical emitters 14 produce and emit light having a wavelength or wavelengths that are employed by chamberless detector 12. In the illustrated embodiment there are two optical emitters 14, with each optical emitter producing a peak wavelength of light. In an embodiment, a first optical emitter 14 can produce an infrared light and a second optical emitter 14 can produce a blue light. The infrared light can have a peak wavelength between 800-950 nm, but in some embodiments may be outside of this range. The blue light can have a peak wavelength between 460-480 nm, but in some embodiments may be outside of this range. In some embodiments, optical emitters 14 can produce wavelengths of light in the infrared, visible, and ultraviolet bands of light. In these other embodiments, optical emitters 14 can produce a wide range of wavelengths of light. For example, in an embodiment, one or more optical emitters 14 can produce violet or ultraviolet light having a wavelength shorter than 460 nm. In another embodiment, one or more optical emitters 14 can produce visible light having a wavelength between 380-700 nm. In yet other embodiments, one or more optical emitters 14 can produce infrared light having a wavelength greater than 700 nm. In some embodiments, optical emitters 14 can produce the same wavelength of light. In some embodiments, only one optical emitter 14 can be used. In other embodiments, three or more optical emitters 14 can be used. In the illustrated embodiment, optical emitters 14 are light emitting diodes (LEDs). In other embodiments, optical emitters 14 can produce light by any suitable means.

Referring again to FIG. 1, optical emitter 14 produces and emits light as emitting cone 22. Emitting cone 22 is an expanding cone of light that is emitted from optical emitter 14 at one or more wavelengths of light. In the illustrated embodiment, two optical emitters 14 are shown but for simplicity of illustration, only one emitting cone 22 is illustrated being emitted from a first optical emitter. It should be recognized that each optical emitter 14 will produce and emit a separate emitting cone 22, although they can be placed adjacent to each other and therefore have overlapping emitting cones 22. In some embodiments, multiple emitting cones 22 can be produced from a single optical emitter 14, and each of the multiple emitting cones 22 can have similar or different optical properties. In the illustrated embodiment, emitting cone 22 is projected into a volume of the space being monitored by covered point sensor 10, with emitting cone 22 having a dispersion angle that results in an expansion of emitting cone 22 at greater distances from optical emitter 14.

Optical sensors 16 detect light. Two optical sensors 16 are depicted in the present embodiment. In some embodiments, one optical sensor 16 can be used. In other embodiments, three or more optical sensors 16 can be used. In the illustrated embodiment, optical sensors 16 are photo diodes. In other embodiments, optical sensors 16 can be any suitable device that produces a photoelectric indication of light. In other embodiments, a single optical sensor 16 can be used, or three or more optical sensors 16 can be used. In some embodiments, the two or more optical sensors 16 can be the same style of photo detector, or can be different styles of photo detectors from each other. In some embodiments, each optical sensor 16 can be responsive to a particular wavelength of light.

Each optical sensor has a corresponding receiving cone 23, depicting the field of view of the particular optical sensor 16, with a single receiving cone 23 being shown for ease of illustration. Receiving cone 23 is an expanding cone defining the region that optical sensor 16 is sensitive to. In some embodiments, a particular optical sensor 16 can have two or more optical cones 23, and each particular optical cone can have different geometries and/or be responsive to different wavelengths of light.

The volume where a particular emitting cone 22 and a particular receiving cone 23 overlap is referred to as a sensing volume. One or more sensing volumes can be created by the interaction of a single emitting cone 22 with a single receiving cone 23, the interaction of a single emitting cone 22 with two or more receiving cones 23, by the interaction of two or more emitting cones 22 with a single receiving cone 23, or by the interaction of two or more emitting cones 22 with two or more receiving cones 23. In the illustrated embodiment, protective cover 30 is transparent. Accordingly, any of the multiple sensing volumes created by covered point sensor 10 as described above can be entirely in inside region 29, outside region 31, or in both inside region 29 and outside region 31. In some embodiments there can be fluid communication from the region outside protective cover 30 to inside protective cover 30.

As shown in FIG. 1, exemplary near particles 24 are located in inside region 29, and exemplary far particles 26 are located in outside region 31. As will be described in FIGS. 2-8, various embodiments of protective cover 30 are available to allow for fluid communication between outside region 31 and inside region 29. Exemplary near particles 24 are located in inside region 29, and exemplary far particles 26 are located in outside region 31. Generally speaking, particulates, including smoke and other airborne particles, can vary in size depending on several factors including without limitation the materials that are smoldering, burning, or combusting, the temperature of the process, the stage of the process, and the concentration of oxygen and other gasses at the point of the process. The process can be combustion, pre-combustion, or any other process that evolves airborne particulates. Moreover, processes other than combustion can cause airborne particulates. For example, chemical reactions can evolve airborne particulates. Particulates can generally range in size from 0.1-2.0 µm in diameter, however they can be smaller in size than 0.1 µm in diameter, or larger in size than 2.0 µm in diameter. Some particulates can be up to 10 µm in diameter. In some embodiments, covered point sensor 10 can monitor for indoor air quality, while being able to discriminate between fine particles (particle sizes≤2.5 µm) and coarse particles (particle sizes≤10 µm).

As described above, each optical sensor 16 has receiving cone 23. The geometry of each receiving cone 23 depends on the field of view, position, and alignment of respective optical sensor 16. Accordingly, the intersection of receiving cone 23 of optical sensor 16, and emitting cone 22 of optical emitter 14, determines the sensing volume, as described above. In a typical embodiment, multiple sensing volumes are created by covered point sensor 10, with each sensing volume determining where particulates can be detected. Covered point sensor 10 detects the presence of particulates by the scattering of light in each of the sensing volumes, as described above. As light illuminates near particles 24 and/or far particles 26, scattering and/or fluorescence occurs. Some of the scattered and/or fluoresced light within each sensing volume is directed to optical sensor 16. The light received by optical sensor 16 causes an electrical reaction in optical sensor 16 which is amplified and analyzed by detection circuitry (not shown) within covered point sensor 10. Accordingly, the electrical signal produced by each optical sensor 16 is received by circuitry (not shown) of covered point sensor 10, thereby producing a sensing event. The processing of these electrical signals that are produced by sensing events can be referred to as monitoring, as described above. During the monitoring process, one or more levels produced by the monitor can be displayed on an indicator and/or recorded on a data storage medium. Moreover, different monitored levels can be produced in response to various detection wavelengths and other factors. The covered point sensor 10 can be programmed to discriminate between various sensing events, while producing additional responses if various threshold criteria are met. Non-limiting examples of additional responses can include activating an alarm, triggering other system responses, and initiating protective actions.

As will be described in FIGS. 2-8, several factors can influence the ability of particulates to enter inside region 29, thereby being detectable in sensing volumes in inside region 29. Similarly, several factors can affect the ability of covered point sensor 10 to detect particulates in outside region 31. Non-limiting examples of these several factors include the size and shape of protective cover 30, the transparency of protective cover 30, the use of mesh/openings/slots/openings on protective cover 30, and the degree of fluid communication from outside region 31 to inside region 29.

Mounting rim 20 surrounds the outer peripheral edge of chamberless detector 12 in the region where protective cover 30 attaches to chamberless detector 12. Similarly, protective cover rim 32 surrounds the outer peripheral edge of protective cover 30 in the region where protective cover 30 attaches to chamberless detector 12. In the illustrated embodiment, mounting rim 20 fully surrounds chamberless detector 12, and protective cover rim 32 fully surrounds protective cover 30, and a removable adhesive can be used to affix protective cover rim 32 to mounting rim 20, thereby affixing protective cover 30 to chamberless detector 12. In other embodiments, a means of fastening protective cover 30 to chamberless detector 12 may be provided. For example, threaded fasteners could be used to affix protective cover 30 to chamberless detector 12. In some embodiments, a distinctive mounting rim 20 may not exist on chamberless detector 12, and/or a distinctive protective cover rim 32 may not exist on protective cover 30. In these embodiments, any suitable means of affixing protective cover 20 to chamberless detector 12 may be employed. Non-limiting examples include friction-fit, snap-fit, twist lock, touch fasteners, threaded fasteners, and permanent adhesives. In other embodiments, mounting rim 20 may only partially surround chamberless detector 12, and/or protective cover rim 32 may only partially surround mounting rim 30. In these other embodiments, for example, tabs, hooks, snaps, feet, or the like may take the place of affixing protective cover 32 to mounting rim 20.

FIGS. 2-8 disclose various embodiments of protective cover 30 as shown in FIG. 1. In the description of FIGS. 2-8, references to emitting cone 22, receiving cone 23, near particles 24, far particles 26, inside region 29, and outside region 31 will be as shown in FIG. 1.

Figure 2:
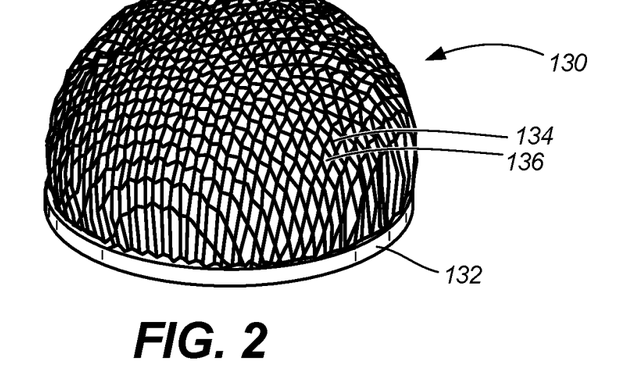
FIG. 2 is a perspective view of a second embodiment of the protective cover.

FIG. 2 is a perspective view of a second embodiment of the protective cover of covered point sensor 10. Shown in FIG. 2 are protective cover 130, protective cover rim 132, protective cover material 134, and protective cover apertures 136. Protective cover 130 is formed from a structure of protective cover material 134, with a lattice of protective cover apertures 136 in the non-material regions. In the illustrated embodiment, protective cover material 134 includes stands of wire that are woven together and formed into the dome-like structure of protective cover 130. In other embodiments, protective cover material 134 can be any metallic or non-metallic material, with non-limiting examples including glass, plastic, fiberglass, resin, and metal. In the illustrated embodiment, protective cover material 134 is anti-reflective, such that light from emitting cone 22 is not reflected within protective cover 130. In other embodiments, protective cover material 134 can be transparent, reflective, anti-reflective, and/or absorptive.

In the illustrated embodiment, protective cover apertures 136 can allow for light from optical emitters 14 to pass from inside region 29 into outside region 31, thereby illuminating particulates in outside region 31. Protective cover apertures 136 can also allow for scattered light from particulates in outside region 31 to pass from outside region 31 to inside region 29, thereby entering one or more receiving cones 23 of optical sensors 16. Accordingly, one or more sensing volumes can be created in outside region 31. Protective cover apertures 136 can also permit fluid communication between outside region 31 and inside region 29, thereby allowing particulates to enter inside region 29. Particles in inside region 29 can be detected by covered point sensor in one or more sensing volumes that are created in inside region 29. In the illustrated embodiment, protective cover material 134 covers between about 1-3% of the surface area of protective cover 130. In some embodiments, protective cover material 134 can cover less than 1% of the surface area of protective cover 130. In yet other embodiments, protective cover material 134 can cover more than 3% of the surface area of protective cover 130.

Figure 3:
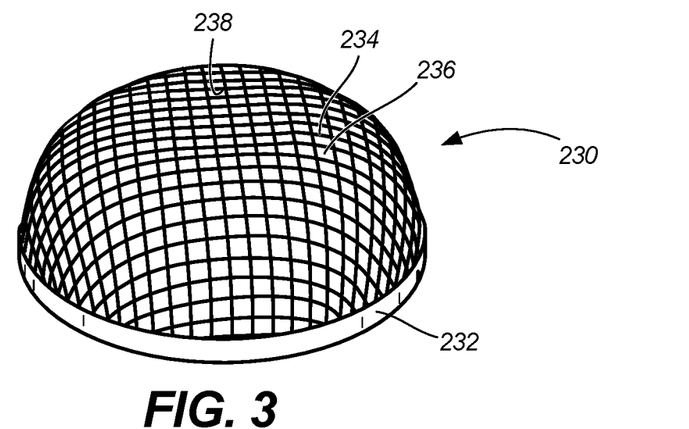
FIG. 3 is a perspective view of a third embodiment of the protective cover.

FIG. 3 is a perspective view of a third embodiment of the protective cover of covered point sensor 10. Shown in FIG. 3 are protective cover 230, protective cover rim 232, protective cover material 234, protective cover apertures 236, and protective cover inner surface 238. Protective cover 230 is formed from a structure of protective cover material 234, with a lattice of protective cover apertures 236 in the non-material regions. In the illustrated embodiment, protective cover material 234 is a lattice structure of metal that is formed into the dome-like structure of protective cover 230. In other embodiments, protective cover material 234 can be any metallic or non-metallic material, with non-limiting examples including plastic, fiberglass, and resin. The lattice of protective cover material 234 can be formed by punching, drilling, etching, or burning protective cover apertures 236 into protective cover material 234. In the illustrated embodiment, protective cover inner surface 238 is anti-reflective, such that light from emitting cone 22 is not reflected within protective cover 230. In other embodiments, protective cover inner surface 238 can be reflective or partially reflective. In some embodiments, protective cover material 234 can be transparent, reflective, anti-reflective, and/or absorptive. Protective cover apertures 236 can function similar to protective cover apertures 136 described in FIG. 1.

Figure 4:
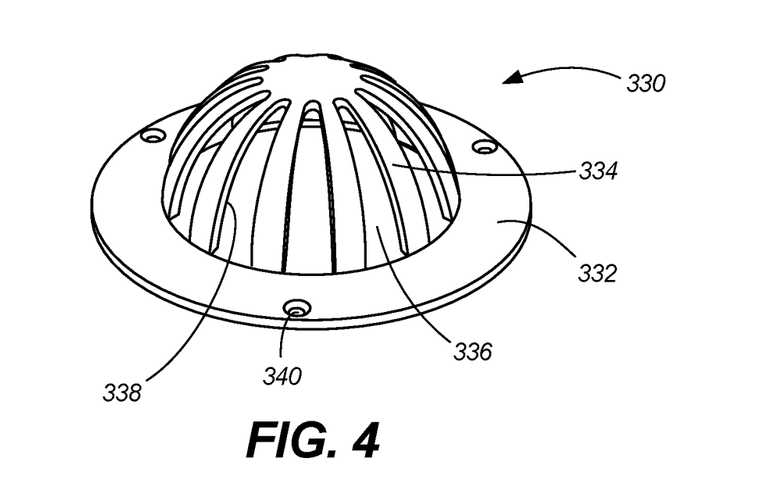
FIG. 4 is a perspective view of a fourth embodiment of the protective cover.

FIG. 4 is a perspective view of a fourth embodiment of the protective cover of covered point sensor 10. Shown in FIG. 4 are protective cover 330, protective cover rim 332, protective cover material 334, protective cover apertures 336, protective cover inner surface 338, and protective cover rim apertures 340. Protective cover 330 is formed from a structure of protective cover material 334, with a structure of protective cover apertures 336 in the non-material regions. In the illustrated embodiment, protective cover material 334 is a material structure of plastic that is molded into the dome-like structure of protective cover 330. In other embodiments, protective cover material 334 can be any metallic or non-metallic material, with non-limiting examples including metal, fiberglass, and resin. In the illustrated embodiment, protective cover apertures 336 are molded into protective cover 330. In other embodiments, protective cover apertures 336 can be formed by punching, cutting, etching, or burning protective cover apertures 336 into protective cover material 334. In the illustrated embodiment, protective cover inner surface 338 is anti-reflective, such that light from emitting cone 22 is not reflected within protective cover 330. In other embodiments, protective cover inner surface 338 can be reflective or partially reflective. In some embodiments, protective cover material 334 can be transparent, reflective, anti-reflective, and/or absorptive.

Protective cover apertures 336 can function similar to protective cover apertures 136 described in FIG. 1. In the illustrated embodiment, protective cover material 334 covers between about 40-60% of the surface area of protective cover 330. In some embodiments, protective cover material 334 can cover less than 40% of the surface area of protective cover 330. In yet other embodiments, protective cover material 334 can cover more than 60% of the surface area of protective cover 330. Protective cover rim apertures 340 can be used for affixing protective cover 330 to mounting rim 20 by the use of mechanical fastening devices. Non-limiting examples of mechanical fastening devices include pins, threaded fasteners, studs, and rivets.

Figure 5:
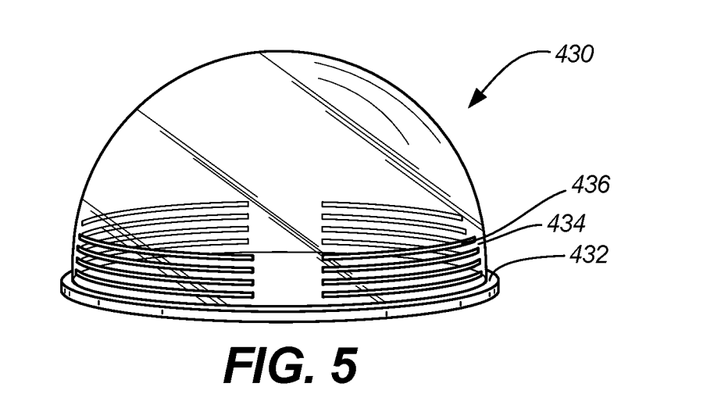
FIG. 5 is a perspective view of a fifth embodiment of the protective cover.

FIG. 5 is a perspective view of a fifth embodiment of the protective cover of covered point sensor 10. Shown in FIG. 5 are protective cover 430, protective cover rim 432, protective cover material 434, and protective cover apertures 436. Protective cover 430 is formed from protective cover material 434, with an array of protective cover apertures 436 that are arranged as parallel latitudes in some regions of protective cover 430. In the illustrated embodiment, protective cover material 434 is transparent plastic material in the form of a dome-like structure for protective cover 430. Accordingly, protective cover 430 can allow light transmission similar to that described in FIG. 1. As use in this disclosure, transparent is defined to mean the material has a transparency of at least 90% at the wavelength or wavelengths of light being transmitted through protective cover 430. In other embodiments, protective cover material 434 can be any transparent or substantially transparent material such as glass or resin. In yet other embodiments, protective cover material 434 can be a partially transparent material. As use in this disclosure, partially transparent is defined to mean the material has a transparency of 40-90% at the wavelength or wavelengths of light being transmitted. In some embodiments, protective cover material 434 can be transparent, reflective, anti-reflective, and/or absorptive.

Protective cover apertures 436 can be formed by molding, punching, cutting, etching, or burning protective cover material 434. Protective cover apertures 436 can function similar to protective cover apertures 136 described in FIG. 1. In the illustrated embodiment, protective cover apertures 436 are arranged as parallel latitudes. In other embodiments, the shape, size, and orientation of protective cover apertures 436 can be of any geometry. In the illustrated embodiment, protective cover apertures 436 cover between about 2-10% of the surface area of protective cover 430. In some embodiments, protective cover apertures 436 can cover less than 2% of the surface area of protective cover 430. In yet other embodiments, protective cover apertures 436 can cover more than 10% of the surface area of protective cover 430. Protective cover apertures 436 can function similar to protective cover apertures 136 described in FIG. 1.

Figure 6:
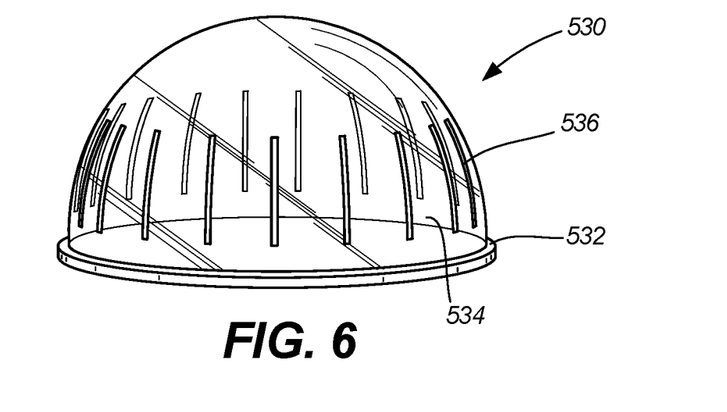
FIG. 6 is a perspective view of a sixth embodiment of the protective cover.

FIG. 6 is a perspective view of a sixth embodiment of the protective cover of covered point sensor 10. Shown in FIG. 6 are protective cover 530, protective cover rim 532, protective cover material 534, and protective cover apertures 536. Protective cover 530 is formed from protective cover material 534, with an array of protective cover apertures 536 that are arranged as meridian longitudes in some regions of protective cover 530. Protective cover apertures 536 can be formed by molding, punching, cutting, etching, or burning protective cover material 534. In the illustrated embodiment, protective cover apertures 536 are arranged as meridian longitudes. In other embodiments, the shape, size, and orientation of protective cover apertures 536 can be of any geometry. In the illustrated embodiment, protective cover material 534 is transparent plastic material in the form of a dome-like structure for protective cover 530. In other embodiments, protective cover material 534 can be any transparent material such as glass, polymer, or resin. In yet other embodiments, protective cover material 534 can be a partially transparent material. In the illustrated embodiment, protective cover material 534 is transparent. Accordingly, protective cover 430 can allow light transmission similar to that described in FIG. 1. In some embodiments, protective cover material 334 can be transparent, reflective, anti-reflective, and/or absorptive.

In the illustrated embodiment, protective cover apertures 536 cover between about 2-10% of the surface area of protective cover 530. In some embodiments, protective cover apertures 536 can cover less than 2% of the surface area of protective cover 530. In yet other embodiments, protective cover apertures 536 can cover more than 10% of the surface area of protective cover 530. Protective cover apertures 536 can function similar to protective cover apertures 136 described in FIG. 1.

Figure 7:
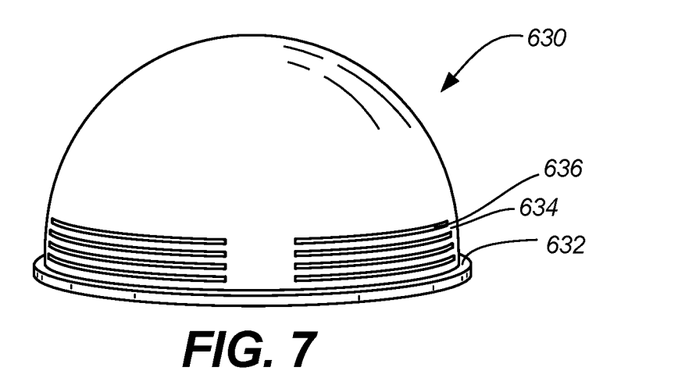
FIG. 7 is a perspective view of a seventh embodiment of the protective cover.

FIG. 7 is a perspective view of a seventh embodiment of the protective cover of covered point sensor 10. Shown in FIG. 7 are protective cover 630, protective cover rim 632, protective cover material 634, and protective cover apertures 636. Protective cover 630 is formed from protective cover material 634, with an array of protective cover apertures 636 that are arranged as parallel latitudes in some regions of protective cover 630. In the illustrated embodiment, protective cover material 634 is an opaque material in the form of a dome-like structure for protective cover 630. As use in this disclosure, opaque is defined to mean the material has a transparency less than of 40% at the wavelength or wavelengths of light being transmitted.

In other embodiments, protective cover material 634 can be any opaque material such as resin or metal. In yet other embodiments, protective cover material 634 can be a partially opaque material. Protective cover apertures 636 can be formed by molding, punching, cutting, etching, or burning protective cover material 634. In the illustrated embodiment, protective cover material 634 is opaque, thereby preventing or restricting the transmission of light from emitting cone 22 to pass through protective cover 630. The opacity of protective cover material 634 can also prevent or restrict the transmission of light from outside region 31 into inside region 29. Sources of light from outside region 31 can include light from optical emitters that is scattered from particulates in outside region 31, or from ambient light external to covered point sensor 10. Non-limiting examples of ambient light can include light sources in the vicinity of covered point sensor such as office, room, and cargo bay lighting, or from direct or reflected light from other sources such as sunlight. These various sources of ambient light can be broad or narrow bands of light in the range of wavelengths from about 300-3000 nm. Protective cover apertures 636 can also allow fluid communication of particulates from outside region 31 into inside region 29, as described earlier.

In the illustrated embodiment, protective cover apertures 636 are arranged as parallel latitudes. In other embodiments, the shape, size, and orientation of protective cover apertures 636 can be of any geometry. Protective cover apertures 636 can allow for light from optical emitters 16 to pass from inside region 29 to outside region 31, and from outside region 31 to inside region 29, thereby allowing for sensing volumes to be created in outside region 31. As described earlier, several factors determine the size and location of the sensing volumes that are created by covered point sensor 10 including the location, direction, and cone width of emitting cones 22 and receiving cones 23. In the illustrated embodiment, protective cover apertures 636 cover between about 2-10% of the surface area of protective cover 630. In some embodiments, protective cover apertures 636 can cover less than 2% of the surface area of protective cover 630. In yet other embodiments, protective cover apertures 636 can cover more than 10% of the surface area of protective cover 630.

Figure 8:
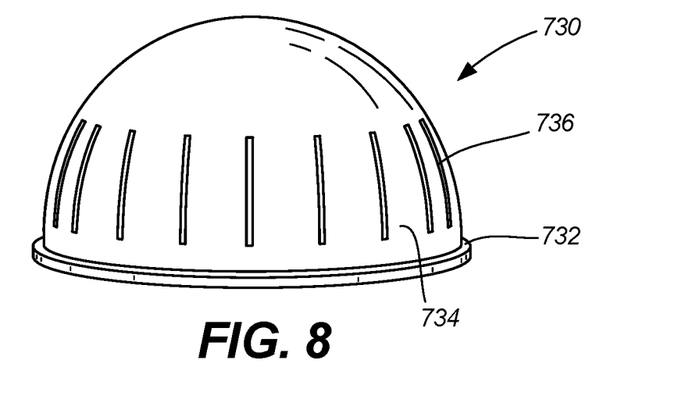
FIG. 8 is a perspective view of an eighth embodiment of the protective cover.

FIG. 8 is a perspective view of an eighth embodiment of the protective cover of covered point sensor 10. Shown in FIG. 8 are protective cover 730, protective cover rim 732, protective cover material 734, and protective cover apertures 736. Protective cover 730 is formed from protective cover material 734, with an array of protective cover apertures 736 that are arranged as meridian longitudes in some regions of protective cover 730. In the illustrated embodiment, protective cover material 734 is an opaque material in the form of a dome-like structure for protective cover 730. In other embodiments, protective cover material 734 can be any opaque material such as resin or metal. In yet other embodiments, protective cover material 734 can be a partially opaque material. Protective cover apertures 736 can be formed by molding, punching, cutting, etching, or burning protective cover material 734. In the illustrated embodiment, protective cover material 734 is opaque, thereby not allowing light from emitting cone 22 to pass through protective cover 730. In the illustrated embodiment, protective cover apertures 736 are arranged as meridian longitudes. In other embodiments, the shape, size, and orientation of protective cover apertures 736 can be of any geometry. In the illustrated embodiment, protective cover apertures 736 cover between about 2-10% of the surface area of protective cover 730. In some embodiments, protective cover apertures 736 can cover less than 2% of the surface area of protective cover 730. In yet other embodiments, protective cover apertures 736 can cover more than 10% of the surface area of protective cover 730. Protective cover apertures 736 can function similar to protective cover apertures 636 described in FIG. 7.

The various embodiments of protective cover 30 depicted in FIGS. 1-8 are non-limiting, with the scope of the present disclosure including any embodiment of a cover that is disposed on chamberless detector 12. While the various embodiments that are disclosed herein generally depict protective cover 30 as being round and symmetrical in shape, other geometries of protective cover 30 are within the scope of the present disclosure. Moreover, the various embodiments that are disclosed herein generally depict protective cover 30 as entirely covering chamberless detector 12, with apertures generally having a uniform distribution. However, a partial protective cover 30 is within the scope of the present disclosure. Moreover, aperture arrangements that are non-uniform in size and/or shape and/or coverage are also within the scope of the present disclosure.

Discussion of Possible Embodiments

The following are non-exclusive descriptions of possible embodiments of the present invention.

A covered chamberless particulate detector comprises a chamberless detector configured to produce a signal when particulate sensing events occurs, one or more optical emitters disposed on the chamberless detector and configured to emit one or more emitting cones of light, one or more optical sensors disposed on the chamberless detector defining one or more receiving cones, and a protective cover disposed on the chamberless detector and defining an inside region and an outside region, wherein each of the one or more optical sensors is configured to detect occurrence of the particulate sensing events.

The covered chamberless particulate detector of the preceding paragraph can optionally include, additionally and/or alternatively, any one or more of the following features, configurations and/or additional components:

A further embodiment of the foregoing covered chamberless particulate detector, wherein each of the one or more emitting cones of light is configured to overlap with each of the one or more receiving cones, thereby creating one or more sensing volumes.

A further embodiment of the foregoing covered chamberless particulate detector, further configured to create one or more of the sensing volumes in the inside region.

A further embodiment of the foregoing covered chamberless particulate detector, further configured to create one or more of the sensing volumes in the outside region.

A further embodiment of the foregoing covered chamberless particulate detector, wherein the one or more optical emitters comprises two optical emitters, each configured to emit a different wavelength of light.

A further embodiment of the foregoing covered chamberless particulate detector, wherein the one or more optical sensors comprises two optical sensors, each configured to detect a different wavelength of light.

A further embodiment of the foregoing covered chamberless particulate detector, wherein the protective cover comprises a material that has a transparency of at least 40%.

A further embodiment of the foregoing covered chamberless particulate detector, wherein the protective cover has a plurality of apertures therethrough, the apertures configured to: permit light from each of the one or more emitting cones of light to illuminate the outside region; permit light from the outside region to enter the inside region; and permit fluid communication between the outside region and the inside region.

A further embodiment of the foregoing covered chamberless particulate detector, wherein the plurality of apertures are configured in a geometrical pattern selected from the group consisting of: parallel latitudes and meridian longitudes.

A further embodiment of the foregoing covered chamberless particulate detector, wherein a ratio of a surface area of the apertures to a total surface area of the protective cover is at least 40%.

A further embodiment of the foregoing covered chamberless particulate detector, wherein the protective cover comprises a material that is selected from the group consisting of: glass, plastic, polymer, fiberglass, resin, and metal.

A further embodiment of the foregoing covered chamberless particulate detector, wherein an inside surface of the protective cover has a reflectivity that is less than 4%.

A further embodiment of the foregoing covered chamberless particulate detector, further comprising a protective cover rim, the protective cover rim disposed on the protective cover in a region where the protective cover matingly attaches to the chamberless detector.

A further embodiment of the foregoing covered chamberless particulate detector, further comprising a plurality of protective cover rim apertures disposed on the protective cover rim, the protective cover rim apertures configured to receive a connector for attaching the protective cover to the chamberless detector.

A further embodiment of the foregoing covered chamberless particulate detector, wherein A method of using a covered chamberless particulate detector that comprises one or more optical emitters, one or more optical sensors, and a protective cover over the optical emitters and the optical sensors that defines an inside region and an outside region. The method includes emitting one or more emitting cones of light from the one or more optical emitters; receiving light in one or more receiving cones by the one or more optical sensors; and detecting particulate sensing events, and producing a signal denoting occurrence of the particular sensing events, based on presence of particulate material in one or more sensing volumes defined by an overlap of the one or more emitting cones of light and the one or more receiving cones; wherein the one or more sensing volumes are located in the inside region, the outside region, or both the inside region and the outside region.

The method of the preceding paragraph can optionally include, additionally and/or alternatively, any one or more of the following features, configurations and/or additional components:

A further embodiment of the foregoing method, wherein the one or more sensing volumes are created in the inside region.

A further embodiment of the foregoing method, wherein the one or more sensing volumes are created in the outside region.

A further embodiment of the foregoing method, wherein the protective cover has a plurality of apertures therethrough, the apertures configured to: permit light from each of the one or more emitting cones of light to illuminate the outside region; permit light from the outside region to enter the inside region; and permit fluid communication between the outside region and the inside region.

A further embodiment of the foregoing method, wherein a ratio of a surface area of the apertures to a total surface area of the protective cover is at least 97%.

A further embodiment of the foregoing method, wherein the protective cover comprises a material that has a transparency of at least 90%.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A covered chamberless particulate detector for optically detecting particulates, the covered chamberless particulate detector comprising:
   one or more optical emitters disposed on the chamberless detector and configured to emit light directed away from the one or more optical emitters within one or more emitting cones;
   one or more optical sensors disposed on the chamberless detector and configured to detect light directed within a receiving cone toward the one or more optical sensors within one or more receiving cones; and
   a protective cover disposed on the chamberless detector, the protective cover having a plurality of apertures configured to permit fluid communication and light transmission between an outside region and an inside region, wherein an inside surface of the protective cover has a reflectivity that is less than 4%;

wherein the one or more receiving cones intersects the one or more light emitting cones thereby forming two or more sensing volumes, at least one of the two or more sensing volumes located in the inside region, and at least one of the two or more sensing volumes located in the outside region, wherein the one or more optical sensors generates a signal in response to a sensing event caused by a particulate within at least one of the two or more sensing volumes.

2. The covered chamberless particulate detector of claim 1, wherein the one or more optical emitters comprises two optical emitters, each configured to emit a different wavelength of light.

3. The covered chamberless particulate detector of claim 1, wherein the one or more optical sensors comprises two optical sensors, each configured to detect a different wavelength of light.

4. The covered chamberless particulate detector of claim 1, wherein the protective cover comprises a material that has a transparency of at least 40%.

5. The covered chamberless particulate detector of claim 1, wherein the plurality of apertures are configured in a geometrical pattern selected from the group consisting of: parallel latitudes and meridian longitudes.

6. The covered chamberless particulate detector of claim 1, wherein a ratio of a surface area of the apertures to a total surface area of the protective cover is at least 40%.

7. The covered chamberless particulate detector of claim 1, wherein the protective cover comprises a material that is selected from the group consisting of: glass, plastic, polymer, fiberglass, resin, and metal.

8. The covered chamberless particulate detector of claim 1, further comprising a protective cover rim, the protective cover rim disposed on the protective cover in a region where the protective cover matingly attaches to the chamberless detector.

9. The covered chamberless particulate detector of claim 8, further comprising a plurality of protective cover rim apertures disposed on the protective cover rim, the protective cover rim apertures configured to receive a connector for attaching the protective cover to the chamberless detector.

10. A method for optically detecting particulates, the method comprising:

providing a protective cover disposed on a chamberless detector;

permitting, via a plurality of apertures through the protective cover, fluid communication and light transmission between an outside region and an inside region formed by the protective cover and the chamberless detector wherein the plurality of apertures are configured in a geometrical pattern selected from the group consisting of: parallel latitudes and meridian longitudes;

emitting, via one or more optical emitters disposed on a chamberless detector, light directed away from the one or more optical emitters within one or more emitting cones;

detecting, via one or more optical sensors disposed on the chamberless detector, light directed within a receiving cone toward the one or more optical sensors within one or more receiving cones; and wherein the one or more receiving cones intersects the one or more light emitting cones thereby forming two or more sensing volumes, at least one of the two or more sensing volumes located in the inside region, and at least one of the two or more sensing volumes located in the outside region; and generating, via the one or more optical sensors, a signal in response to a sensing events caused by a particulate within at least one of the two or more sensing volumes.

11. The method of claim 10, wherein a ratio of a surface area of the plurality of apertures to a total surface area of the protective cover is at least 97%.

12. The method of claim 10, wherein the protective cover comprises a material that has a transparency of at least 90%.

13. The method of claim 10, wherein the one or more optical emitters comprises two optical emitters, each configured to emit a different wavelength of light.

14. The method of claim 10, wherein the one or more optical sensors comprises two optical sensors, each configured to detect a different wavelength of light.

15. The method of claim 10, wherein the sensing event is caused by light scattered by the particulate.

16. The method of claim 10, wherein the sensing event is caused by light fluoresced by the particulate.

17. A covered chamberless particulate detector for optically detecting particulates, the covered chamberless particulate detector comprising:

one or more optical emitters disposed on the chamberless detector and configured to emit light directed away from the one or more optical emitters within one or more emitting cones;

one or more optical sensors disposed on the chamberless detector and configured to detect light directed within a receiving cone toward the one or more optical sensors within one or more receiving cones; and a protective cover disposed on the chamberless detector, the protective cover having a plurality of apertures configured to permit fluid communication and light transmission between an outside region and an inside region, wherein a ratio of a surface area of the plurality of apertures to a total surface area of the protective cover is at least 97%;

wherein the one or more receiving cones intersects the one or more light emitting cones thereby forming two or more sensing volumes, at least one of the two or more sensing volumes located in the inside region, and at least one of the two or more sensing volumes located in the outside region, wherein the one or more optical sensors generates a signal in response to a sensing event caused by a particulate within at least one of the two or more sensing volumes.

18. The covered chamberless particulate detector of claim 17, wherein an inside surface of the protective cover has a reflectivity that is less than 4%.

19. The covered chamberless particulate detector of claim 17, wherein the protective cover comprises woven strands of wire.

20. The covered chamberless particulate detector of claim 17, wherein the protective cover comprises a metallic lattice structure.

* * * * *